US006261518B1

(12) United States Patent
Caputo et al.

(10) Patent No.: US 6,261,518 B1
(45) Date of Patent: *Jul. 17, 2001

(54) PROCESS AND APPARATUS FOR PLASMA STERILIZING WITH PULSED ANTIMICROBIAL AGENT TREATMENT

(75) Inventors: Ross A. Caputo, Long Grove; Thomas J. Amsler, Grayslake; Kangyan Du, Vernon Hills; Jeffery Jones, Antioch, all of IL (US); Kern A. Moulton, Reno, NV (US); Bryant A. Campbell, deceased, late of Los Gatos, CA (US), by Louise A. Campbell, legal representative

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/183,775

(22) Filed: Oct. 30, 1998

Related U.S. Application Data

(63) Continuation of application No. 08/861,956, filed on May 22, 1997, now abandoned, which is a continuation of application No. 08/461,412, filed on Jun. 5, 1995, now Pat. No. 5,645,796, which is a continuation-in-part of application No. 08/266,129, filed on Jun. 27, 1994, now abandoned, which is a division of application No. 08/065,859, filed on May 21, 1993, now Pat. No. 5,413,758, which is a continuation-in-part of application No. 07/749,041, filed on Aug. 27, 1991, now Pat. No. 5,244,629, which is a continuation-in-part of application No. 07/576,235, filed on Aug. 31, 1990, now Pat. No. 5,084,239.

(51) Int. Cl.$^7$ ................................ A61L 2/14; A61L 2/20

(52) U.S. Cl. ........................... 422/22; 422/23; 422/28; 422/292; 422/906; 422/907; 250/455.11

(58) Field of Search ................... 422/21–23, 28, 422/33, 36, 37, 906, 907, 292; 250/424, 455.11, 492; 204/164

(56) References Cited

U.S. PATENT DOCUMENTS

| | | |
|---|---|---|
| 3,383,163 | 5/1968 | Menashi . |
| 3,410,776 | 11/1968 | Bersin . |
| 3,428,548 | 2/1969 | Hollahan . |
| 3,704,096 | 11/1972 | Verses et al. . |
| 3,737,608 | 6/1973 | Nagao et al. . |
| 3,851,436 | 12/1974 | Fraser et al. . |
| 3,948,601 | 4/1976 | Fraser et al. . |
| 4,065,369 | 12/1977 | Ogawa et al. . |
| 4,123,663 | 10/1978 | Horiike . |
| 4,138,306 | 2/1979 | Niwa . |
| 4,151,034 | 4/1979 | Yamamoto . |
| 4,160,690 | 7/1979 | Shibagaki . |

(List continued on next page.)

Primary Examiner—Terrence R. Till
Assistant Examiner—Theresa T. Snider
(74) Attorney, Agent, or Firm—Barnes & Thornburg

(57) ABSTRACT

A process and equipment for plasma sterilization in which articles in a sterilizing chamber are taken through at least one combination sterilizing cycle. The articles to be sterilized may include the interior of a vessel or chamber. In that case, the vessel or chamber itself may serve as a sterilizing chamber and connects to the plasma generating chamber. Each combination sterilizing cycle includes a pulsed treatment with gaseous antimicrobial agent, removal of the gaseous antimicrobial agent, and a plasma treatment. The pulsed treatment includes one or more pulse-vacuum cycles, each pulse-vacuum cycle includes the steps of evacuating the sterilizing chamber and exposing the article to the gaseous antimicrobial agent with a predetermined pressure profile during a predetermined time. The gaseous antimicrobial agent is preferably carried in a gas mixture with a nonreactive carrier gas. In one embodiment, the predetermined pressure is pulsed. In another embodiment, it is ramped. After the pulsed treatment, the antimicrobial agent is removed by evacuating the sterilizing chamber. The plasma treatment includes exposure of the article to a plasma having essentially uncharged, highly reactive free radicals, molecules and atoms.

29 Claims, 5 Drawing Sheets

U.S. PATENT DOCUMENTS

| | | |
|---|---|---|
| 4,169,123 | 9/1979 | Moore et al. . |
| 4,169,124 | 9/1979 | Forstrom et al. . |
| 4,207,286 | 6/1980 | Boucher . |
| 4,230,663 | 10/1980 | Forstrom et al. . |
| 4,289,728 | 9/1981 | Peel et al. . |
| 4,321,232 | 3/1982 | Bithell . |
| 4,348,357 | 9/1982 | Bithell . |
| 4,366,125 | 12/1982 | Kodera et al. . |
| 4,437,567 | 3/1984 | Jeng . |
| 4,643,876 | 2/1987 | Jacobs et al. . |
| 4,756,882 | 7/1988 | Jacobs et al. . |
| 4,801,427 | 1/1989 | Jacob . |
| 4,818,488 | 4/1989 | Jacob . |
| 4,898,715 | 2/1990 | Jacob . |
| 4,917,586 | 4/1990 | Jacob . |
| 4,931,261 | 6/1990 | Jacob . |
| 4,943,417 | 7/1990 | Jacob . |
| 4,976,920 | 12/1990 | Jacob . |
| 5,244,629 * | 9/1993 | Caputo et al. .......... 422/23 |
| 5,302,343 | 4/1994 | Jacob . |
| 5,413,758 * | 5/1995 | Caputo et al. .......... 422/23 |

* cited by examiner

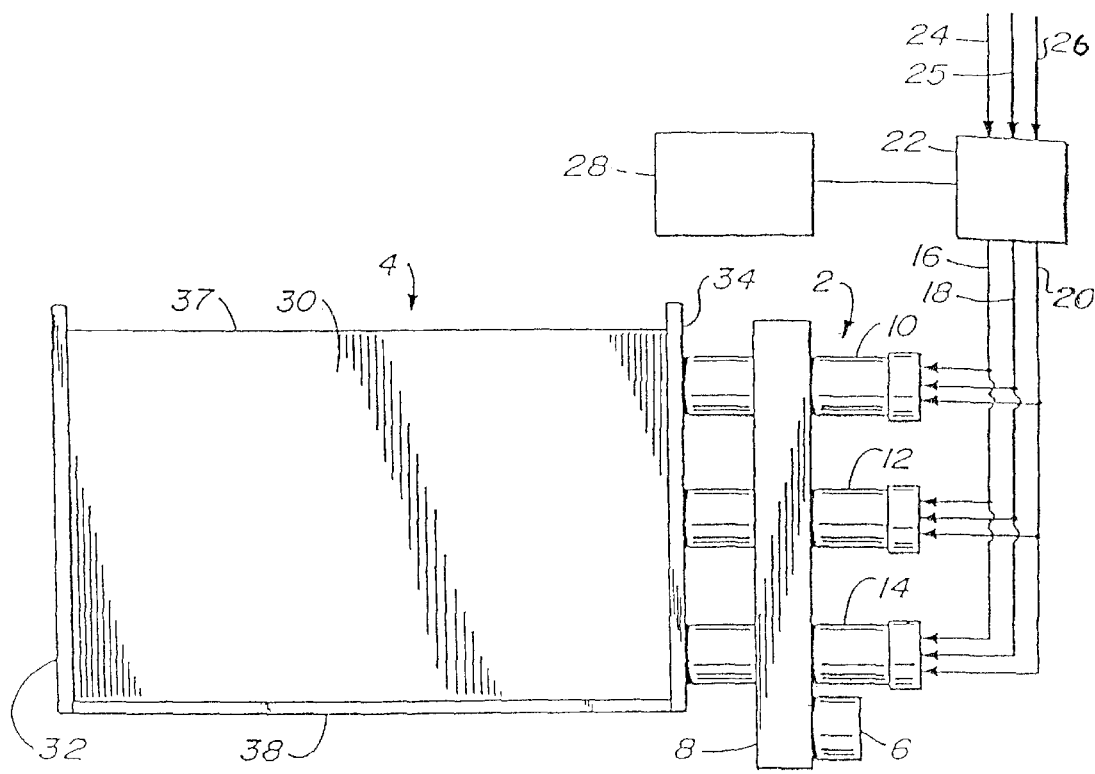
FIG._1
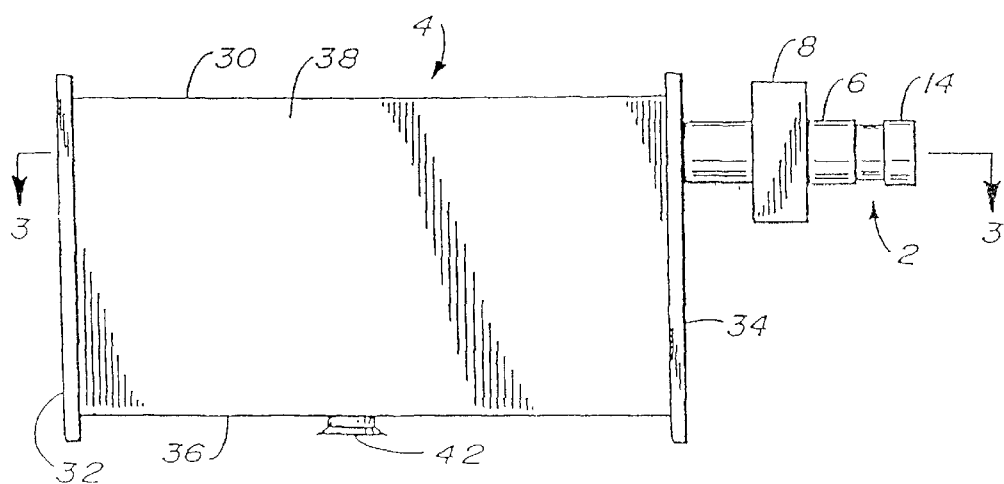
FIG._2

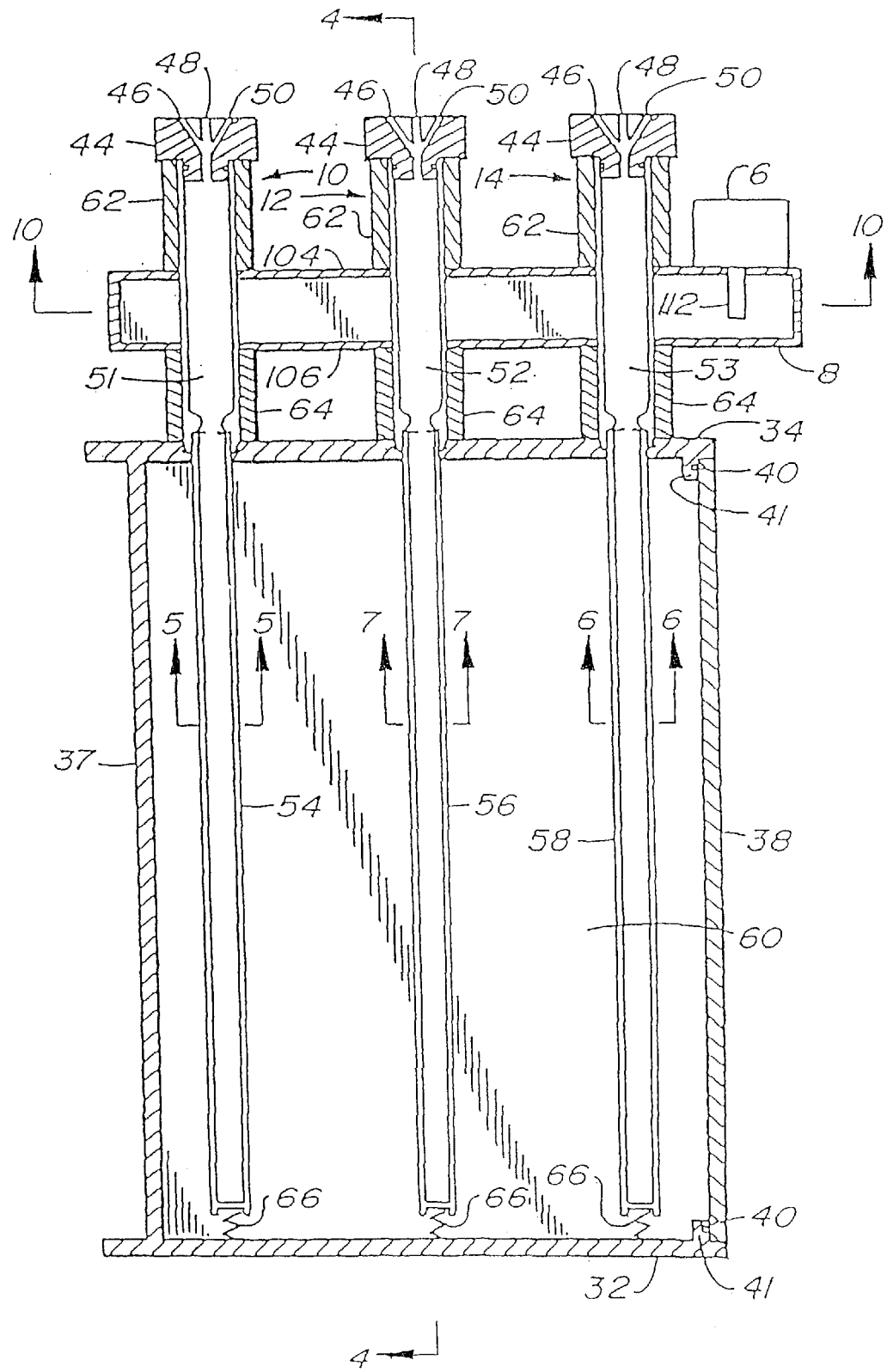
FIG._3

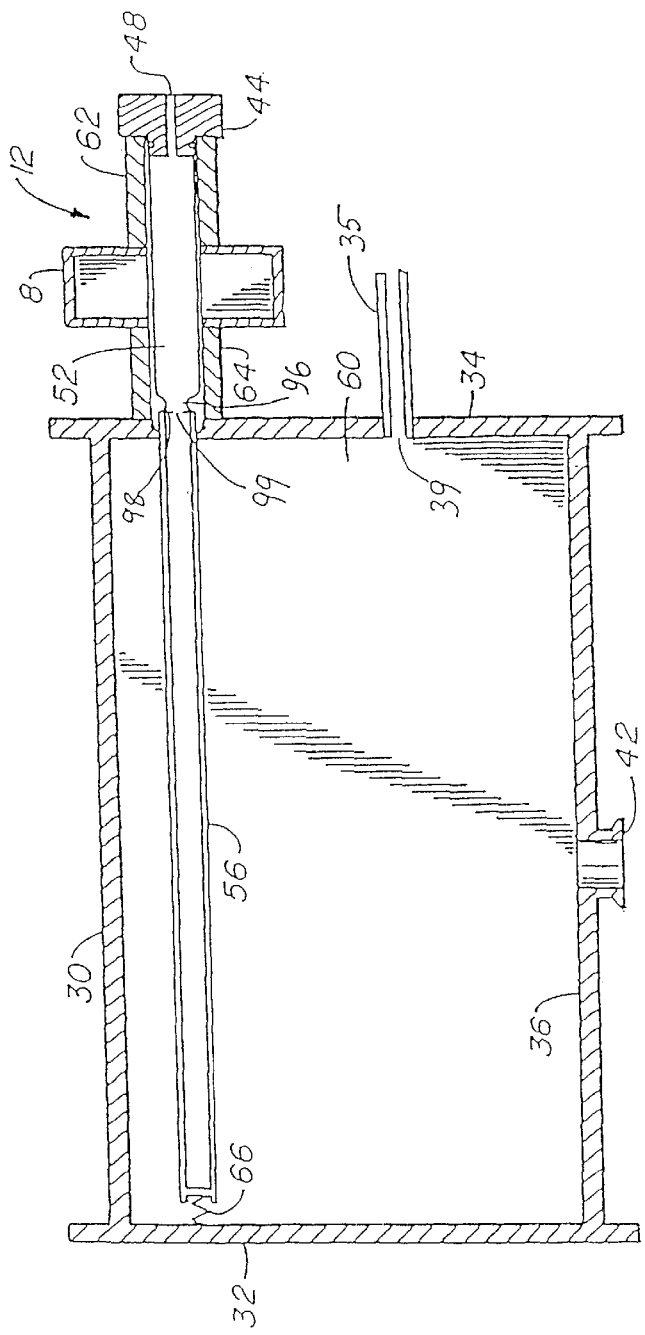
FIG._4
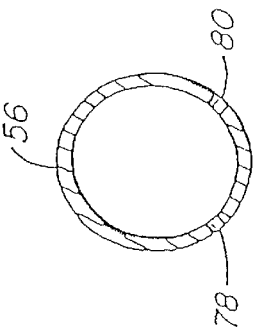
FIG._5
FIG._6
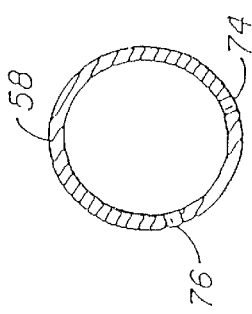
FIG._7

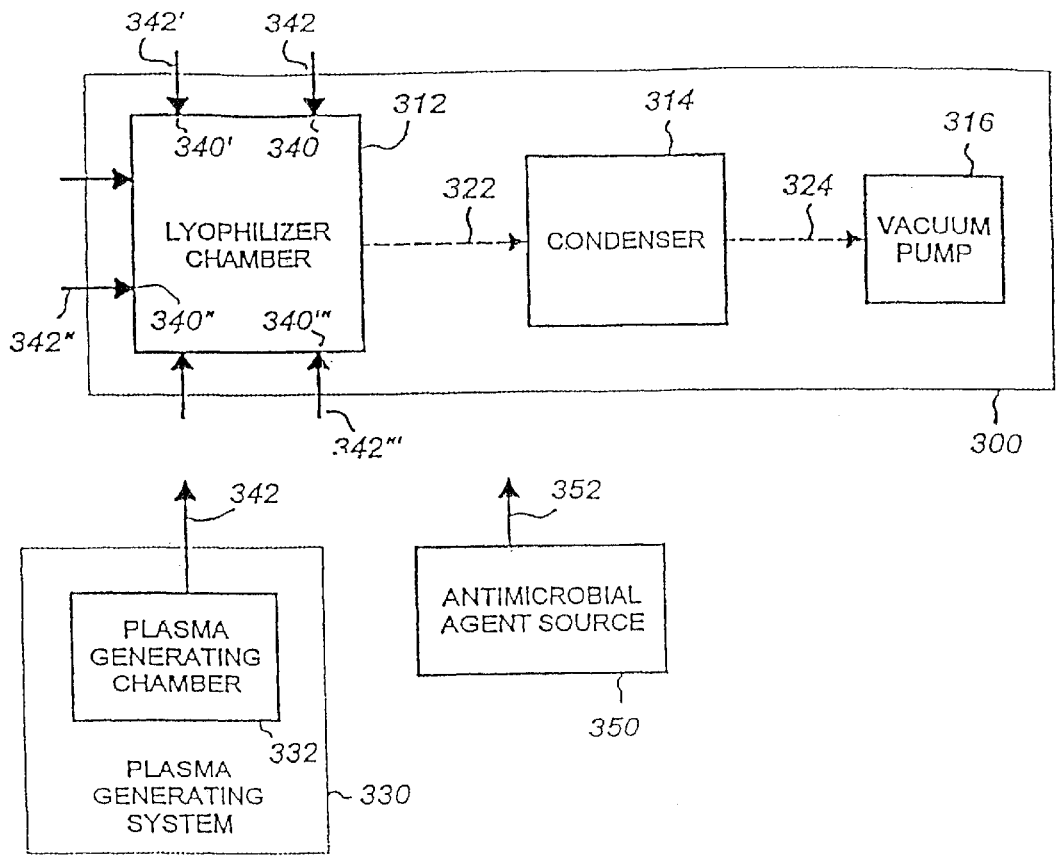
FIG._ 8

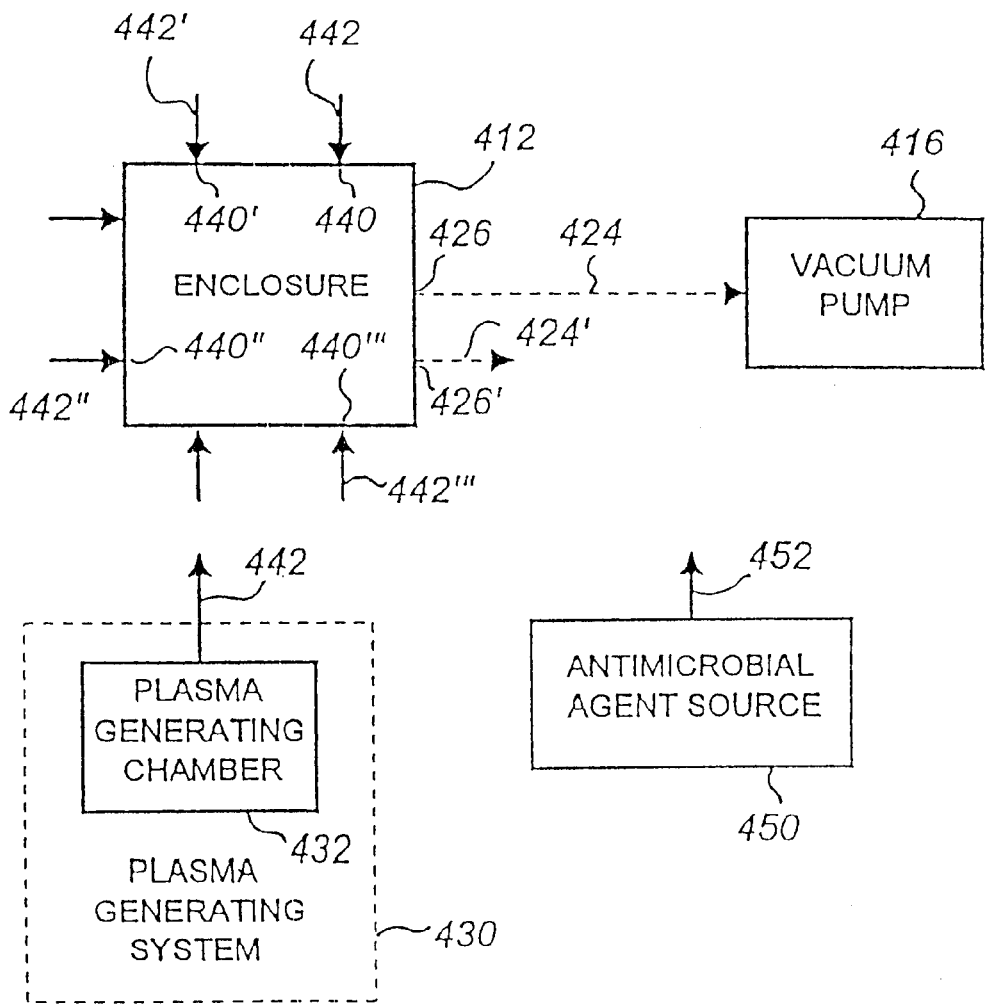
FIG._9

PROCESS AND APPARATUS FOR PLASMA STERILIZING WITH PULSED ANTIMICROBIAL AGENT TREATMENT

This is a continuation of application Ser. No. 08/861,956, filed May 22, 1997, now abn., which is a continuation of application Ser. No. 08/461,412, filed Jun. 5, 1995, now U.S. Pat. No. 5,645,796, which is a continuation-in-part of application Ser. No. 08/266,129, filed Jun. 27, 1994, now abandoned, which is a division of application Ser. No. 08/065,859, filed May 21, 1993, now U.S. Pat. No. 5,413,758, which is a continuation-in-part of application Ser. No. 07/749,041, filed Aug. 27, 1991, now U.S. Pat. No. 5,244,629, which is a continuation-in-part of application Ser. No. 07/576,235, filed Aug. 31, 1990, now U.S. Pat. No. 5,084,239.

FIELD OF THE INVENTION

This invention relates to a plasma sterilization process and apparatus comprising pulsed treatment with a gaseous or vaporized antimicrobial agent such as hydrogen peroxide or a peracid to kill microorganisms and spores on the article. In particular, this invention relates to exposing an article to be sterilized to a plurality of treatment cycles, each cycle including cyclic pulses of a gaseous or vaporized antimicrobial agent at one pressure, followed by pressure reduction to a lower pressure. The article is then exposed to a gas plasma. The article to be sterilized may include a container or enclosure whose interior is required to be sterilized.

BACKGROUND OF THE INVENTION

A variety of gas sterilization methods has been investigated in the past. Methods using ethylene oxide and other disinfecting gases are widely used for sterilizing a wide range of medical products from pharmaceutical preparations to surgical instruments. Irradiation alone or together with disinfecting gases has also been investigated, as summarized by Russell, A. THE DESTRUCTION OF BACTERIAL SPORES. New York: Academic Press (1982).

A sterilizing method must effectively kill all organisms, including spores, without damage to the article or goods being sterilized. However, many disinfecting gases which meet this criterion, such as ethylene oxide and irradiation methods have been recognized to expose workers and the environment to safety hazards. States and Federal legislation are severely restricting the amount of hazardous gases such as ethylene oxide (a carcinogen) in the working environment, or the use of any system or method which produces toxic residues or exhaust products. This is presenting a major crisis in hospitals and other areas of the health industry.

DESCRIPTION OF THE PRIOR ART

Sterilizing plasmas have been generated with a wide variety of gases: argon, helium or xenon (U.S. Pat. No. 3,851,436); argon, nitrogen, oxygen, helium or xenon (U.S. Pat. No. 3,948,601); glutaraldehyde (U.S. Pat. No. 4,207,286); oxygen (U.S. Pat. No. 4,321,232); oxygen, nitrogen, helium, argon or Freon with pulsed pressure (U.S. Pat. No. 4,348,357); hydrogen peroxide (U.S. Pat. Nos. 4,643,876 and 4,756,882); nitrous oxide, alone or mixed with oxygen, helium or argon (Japanese Application Disclosure No. 103460-1983); and nitrous oxide, alone or mixed with ozone (Japanese Application No. 162276-1983). Unfortunately, these plasmas have proven to be too corrosive to articles being sterilized and particular packaging materials; have left toxic residues on the sterilized articles; or have presented safety or environmental hazards.

Typical prior art plasma sterilizing systems such as U.S. Pat. No. 4,643,876 have a combined chamber where both plasma generation and sterilization take place. The plasma is generated from hydrogen peroxide vapor and residue, and the article being sterilized is directly exposed to the plasma inducing electromagnetic field. The in situ generation of the ions and free radicals in the vicinity of the article surface is considered to be a critical part of the static process. Antimicrobial hydrogen peroxide pretreatment has been combined with exposure of the article to the electromagnetic plasma generating environment to remove any remaining hydrogen peroxide residues. The process is static, that is, the plasma is generated in the volume of gas initially in the closed chamber, and the articles are not exposed to plasma generated from a mixture of hydrogen, oxygen and inert gases, as in the process of this invention. These systems tend to rapidly decompose plastic and cellulose containing packages because of the strong oxidizing properties of the ions and free radicals in the elevated temperatures of the process. Limiting the process time to prevent package destruction also produces an inadequate spore kill rate.

Plasma gas sterilizer systems described in U.S. Pat. Nos. 3,851,436 and 3,948,601 comprise separate plasma RF generation chamber and sterilizing chamber. A gas plasma produced in the plasma generating chamber with argon, helium, nitrogen, oxygen or xenon is passed into a separate sterilization vacuum chamber.

Non-plasma gas sterilization procedures have been described using ozone (U.S. Pat. No. 3,704,096) and hydrogen peroxide (U.S. Pat. Nos. 4,169,123, 4,169,124, 4,230,663, 4,366,125, 4,289,728, 4,437,567 and 4,643,876). These materials are toxic or corrosive and leave undesirable residues.

Peracid sterilization processes have been disclosed in East German Patent Application Serial No. 268,396, EPO Patent Application Publication No. 109,352 A1, and U.K. Patent 2,214,081, for example. The sporicidal activities of peracetic acid, alone and in combination with other compounds including ethanol and hydrogen peroxide are disclosed by Leaper, S., Food Microbiology. 1:199–203 (1984); Leaper, S. et al, J. Applied Biol. 64:183–186 (1988); Leaper, S., J. Food Technology. 19:355–360 (1984); and Leaper, S., J. Food Technology. 19:695–702 (1984). These methods are not effective to sterilize the contents of packages containing cellulose and other materials which are reactive with peracid species.

The use of plasma to sterilize containers was suggested in U.S. Pat. No. 3,383,163.

The above apparatus and methods do not achieve complete sterilization for many types of articles requiring sterilization, and most produce damage to articles and packaging in the course of producing high sterilization rates. As a result, they do not achieve the necessary goal of providing an all purpose, effective sterilizing system and process.

OBJECTS AND SUMMARY OF THE INVENTION

It is an object of this invention to provide an improved plasma sterilizing process which carries out effective sterilization quickly, with no toxic residues and with emissions which present no environmental safety hazard and without damage to articles, including those that are packaged or in the form of a container.

It is another object of this invention to provide an economical sterilizing process which is safe and effective for use in a hospital environment.

It is another object of the present invention to provide an efficient process which achieves sterilization with all types of articles used in the health care environment, including metallic articles and articles contained in porous sterilization packaging including cellulosic materials.

It is also another object of the present invention to provide an efficient and cost-effective process for sterilization of vessels or chambers such as lyophilizers or sterile isolation enclosures.

These and additional objects are accomplished by the method of this invention for plasma sterilization which comprises exposing an article in a sterilizing chamber to at least one combination sterilizing cycle. In the case where the article to be sterilized is the interior of a container, the container itself may function as a sterilizing chamber connectable to a plasma source and an antimicrobial source. Each sterilizing cycle is comprised of a pulsed treatment with gaseous antimicrobial agent, removal of the gaseous antimicrobial agent, and a plasma treatment. The pulsed treatment comprises one or more pulse-vacuum cycles, each pulse-vacuum cycle comprising the steps of evacuating the sterilizing chamber and exposing the article to the gaseous antimicrobial agent for a predetermined duration. After the pulsed treatment, the antimicrobial agent is removed by evacuating the sterilizing chamber. The plasma treatment comprises exposing the article to a stream of plasma having essentially uncharged, highly reactive free radicals which are oxidizing or reducing agents. The plasma is generated in a separate plasma generating chamber and is supplied to effect sterilization in the sterilization chamber. The pulsed treatment and the plasma treatment follow a predetermined order in each combination sterilizing cycle.

According to one aspect of the invention, the antimicrobial agent is preferably selected from the group consisting of hydrogen peroxide, a peracid antimicrobial agent, or mixtures thereof, the peracid antimicrobial agent being selected from the group consisting of saturated and unsaturated peralkanoic acids having from 1 to 8 carbon atoms and halogenated derivatives thereof According to another aspect of the invention, the pressure of the gaseous antimicrobial agent is ramped up (i.e. monotonically increased) during the predetermined duration.

According to another aspect of the invention, the gaseous antimicrobial agent is introduced in a gaseous mixture with a nonreactive carrier gas.

According to another aspect of the invention, the gaseous mixture is maintained at substantially a maximum concentration supported by the temperature maintained in the sterilization chamber.

According to yet another aspect of the invention, the gaseous antimicrobial agent in the gaseous mixture has a partial pressure substantially at its saturation vapor pressure supported by the temperature maintained in the sterilization chamber.

According to another aspect of the invention, water vapor is mixed with the gaseous antimicrobial agent to enhance its sterilizing action.

A plasma source gas mixture is ionized into a plasma having ionization products that include highly destructive components in the form of charged particles and ultra-violet radiation. Preferably, sterilization is effected by employing plasma downstream products consisting essentially of uncharged, highly reactive free radicals, atoms and excited molecules of a gas mixture to sterilize articles. A plasma distribution device blocks the ultra-violet radiation and facilitates the recombination of the charged particles such that essentially uncharged, highly reactive free radicals, atoms and excited molecules of the gas mixture are delivered to the articles or vessels to be sterilized.

This combination sterilizing cycle treatment process is particularly suitable for sterilizing a porous article or an article enclosed in a porous container, the container being surrounded by the gas plasma during the treatment, even when the porous container comprises a carbohydrate composition.

According to yet another aspect of the present invention, the article to be sterilized is the interior of a vessel or a chamber and any articles therein. One example of such a chamber would be a sterile isolation enclosure or a lyophilizer which functions as a vacuum chamber for freeze-drying pharmaceutical and medical products. In this application, the lyophilizer chamber is adapted to receive a gas plasma from a plasma generating chamber so that it acts as a sterilization chamber where its interior is to be sterilized. This method is effective and economical since conventional sterilization methods using ethylene oxide or steam have their drawbacks, and the lyophilizer being built as a vacuum chamber expediently allows adaptation to a plasma sterilizer without the expense of a separate vacuum system.

Additional objects, features and advantages of the present invention will be understood from the following description of the preferred embodiments, which description should be taken in conjunction with the accompanying drawings.

BRIEF DESCRIPTION OF THE DRAWINGS

FIG. 1 is a top view of a plasma sterilizer suitable for use in the process of this invention.

FIG. 2 is a front view of the plasma sterilizer embodiment of FIG. 1.

FIG. 3 is a cross-sectional view of the plasma sterilizer embodiment of FIG. 1 and FIG. 2, taken along the line 3—3 in FIG. 2.

FIG. 4 is a cross-sectional view of the plasma sterilizer embodiment of FIG. 3, taken along the line 4—4.

FIG. 5 is a cross-sectional view of tube 54 taken along line 5—5 in FIG. 3.

FIG. 6 is a cross-sectional view of tube 58 taken along line 6—6 in FIG. 3.

FIG. 7 is a cross-sectional view of tube 56 taken along line 7—7 in FIG. 3.

FIG. 8 is a schematic illustration of adapting a lyophilizer for sterilization.

FIG. 9 is a schematic illustration of a general enclosure adapted to be sterilized by the plasma process of the present invention.

DETAILED DESCRIPTION OF THE INVENTION

Hospitals originally relied on disinfectants and steam autoclaves for sterilizing implements. In more recent years, ethylene oxide gas sterilization has made possible the sterilization of heat labile packaged articles, drugs and medical supplies, and hospital systems are highly dependent upon these procedures. However, ethylene oxide is now known to be a dangerous carcinogen, and a number of new state laws protecting worker safety and the environment are precluding further use of ethylene oxide sterilizers in hospital environments.

Numerous gas plasma sterilizers using a wide variety of gases have been described in the literature. A few have been commercially produced. One system described in. U.S. Pat. No. 4,643,876, for example, pretreats the article to be sterilized with hydrogen peroxide before it is placed in the electromagnetic field producing the plasma. It relies on the presence of the hydrogen peroxide in the electromagnetic field as a source of the plasma products and the direct exposure of the hydrogen peroxide to the electromagnetic field to destroy the hydrogen peroxide. This system is suitable only for sterilizing non-metallic articles because of the heating-of metallic articles and the destabilizing effect of metallic articles in plasma generating electromagnetic fields. However, even with hydrogen peroxide pretreatment, complete sterilization is not achieved without severe degradation of the packaging materials.

A few have focused on residue contamination problems. The previously described gas sterilizers either fail to satisfy current regulatory residue and exhaust emission safety standards of several states, because they either leave unacceptable residues, produce exhaust emissions which are potentially hazardous to hospital personnel, or cause unacceptable destruction of packaging materials. Substituting one hazard for another, they are thus not satisfactory for replacing ethylene oxide sterilizers.

Peracids such as peracetic acid are well known as sterilizing agents in situations where their residues can be tolerated or easily removed and where adequate exposure time is allowed. However, peracid vapors are also known to be ineffective for sterilizing goods packaged in the conventional cellulosic sterile packages used in the health care field.

This invention is based on the discovery that pulsed antimicrobial agent pretreatment of both packaged and unpackaged articles, followed by exposure of the articles to sterilizing gas plasmas, reliably and more efficiently kills resistant spores at conditions which are not destructive to packaging materials. The exposure to the gas plasma in a sterilizing chamber separate from the plasma generating system protects the packaging and plastic components and permits the sterilization of metallic articles.

The process of this invention employs a plasma produced from gas mixtures containing essentially oxidizing agents such as oxygen and/or reducing agents such as hydrogen, and optionally other carrier gases such as inert gases. The exhaust gas products fully satisfy current environmental and worker safety concerns, the products of the plasma being almost entirely water vapor, carbon dioxide and non-toxic gases normally found in the atmosphere.

The term "plasma" as used herein is defined to include any portion of the gas or vapors which contain electrons, ions, free radicals, dissociated and/or excited atoms or molecules produced as a result of the applied electric or electromagnetic field including any accompanying radiation which might be produced. The electromagnetic field can cover a broad frequency range, and can be produced by a magnetron, klystron or RF coil. For purposes of clarity of presentation and not by way of limitation, the description hereinafter describes the use of a magnetron as the electromagnetic field source, and the use of all other suitable sources of the electromagnetic field required for plasma production are intended to be included, including without limitation, magnetrons, klystron tubes, RF coils, and the like.

The term "sterilization" connotes a process by which all viable forms of microorganisms are destroyed or removed from an object. Since microorganisms die according to first order chemical kinetics, it is customary to define sterility in terms of "probability of survivors". The practical goal of a sterilization process is therefore measured as a probability (e.g., $10^{-3}$, $10^{-6}$, $10^{-12}$), the probability indicating the lethal effect of a particular sterilizing dose or regimen. It is usual to assume increased time of exposure to a set of sterilizing conditions will decrease the probability of survivors accordingly. Doubling the sterilizing time of identical conditions would result in a doubling of the exponent of the probability term, for example $10^{-3}$ $^6$ would become $10^{-12}$.

The term "pretreatment" is used herein to define that at least one pulsed treatment of the article being sterilized with antimicrobial agent is followed by treatment with gaseous plasma products. The "pretreatment" with antimicrobial agent can follow one or more earlier plasma treatments and can be followed by one or more plasma treatments. Repetitions of the pulsed treatment and plasma gas treatment cycle any number of times can be used until total killing of spores with even the most resistant articles is achieved. The combination of peroxide and/or peracid antimicrobial agent and plasma gas treatments is synergistic in achieving a spore kill rate which exceeds the killing rate which can be achieved by use of hydrogen peroxide or peracid alone, or plasma gases alone, while preserving the integrity of packaging materials. The residues are also entirely eliminated by the plasma gases and vacuum.

The pulsed treatment comprises one or more pulse-vacuum cycles. Each pulse-vacuum cycle preferably begins by evacuating the sterilization chamber. This is followed by exposing the article to be sterilized in the sterilization chamber to gaseous antimicrobial agent at a predetermined pressure for a predetermined period. If the antimicrobial agent exists in a liquid state at room temperature, it is first vaporized. For considerations of stability, ease of transport, and higher operating pressures, the vaporized antimicrobial agent may be carried in a mixture with a nonreactive carrier gas such as an inert or noble gas.

According to one aspect of the invention, water vapor is also mixed with the gaseous antimicrobial agent to enhance its sterilizing action. It has been discovered that with vaporized peracetic acid as the antimicrobial agent, a relative humidity of 20–100% further enhances the effectiveness.

Optionally, the pressure is such that the antimicrobial agent is maintained at substantially the maximum concentration supported by the temperature in the sterilization chamber without occurrence of condensation. Thus the partial pressure of the antimicrobial agent is near the saturation vapor pressure of the antimicrobial agent for the temperature in the sterilization chamber.

In one embodiment, the pressure of the antimicrobial agent and the carrier gas introduced into the sterilization chamber is pulsed. Preferably the pressure pulses are in the range of from 0.1 to 50 torr. This helps to replenish antimicrobial agent consumed by reaction with the article. It also helps to drive the antimicrobial agent into packaging barrier or to diffuse into long lumens of medical devices, such as flexible endoscopes or hypodermic needles.

In another embodiment, the pressure is ramped up (i.e. monotonically increased) during the predetermined exposure period. In general pulsing helps to drive the antimicrobial agent into the article and increasing the pressure with time helps to replenish spent agent. Other pressure profiles having a combination of pulsing and ramping are also possible.

The term "peracid" as used herein, is defined to include well known peracid antimicrobial agents such as saturated and unsaturated peralkanoic acids including peraralkanoic acids having from 1 to 8 carbon atoms and halogenated derivatives thereof. Examples of suitable peracids include known peracetic acid, halogenated peracetic acids, performic acid, perpropionic acid, halogenated perpropionic acids, perbutanoic acid and its halogen derivatives, perisovaleric acid and its halogen derivatives, percapronic acid and its halogen derivatives, percrotonic acid, monopersuccinic acid, monoperglutaric acid, and perbenzoic acid, for example. The halogenated peracids contain one or more chloro, bromo, iodo or fluoro groups. The preferred peracids are sufficiently volatile to form an effective sporicidal vapor concentration at temperatures less than 80° C.

It is to be understood that the operating temperature of the present process is determined by the characteristics of the articles being sterilized, not by temperature limitations of the sterilization process. Many medical articles to be sterilized will not withstand temperatures over 60° C., while other articles such as metallic surgical instruments are more efficiently sterilized at higher temperatures.

In the pulsed treatment using hydrogen peroxide, the article is contacted with hydrogen peroxide vapors produced by completely evaporating 1 to 10 (wt/wt) % hydrogen peroxide solution and preferably from 2 to 8 (wt/wt) % hydrogen peroxide solution. The optimal vapor pretreatment involves contacting the article to be sterilized with hydrogen peroxide vapor in the sterilizing chamber. A total pulsed contact time of from 5 to 30 minutes is usually sufficient to insure contact of the entire surface of a packaged article with the hydrogen peroxide vapor.

In the pulsed treatment with peracid, peracid treatment is effected by contact of the article with antimicrobial concentrations of the peracid vapor. Preferably, the pulsed peracid pretreatment is carried out by exposing the article to be sterilized to peracid vapor produced by completely evaporating from 1 to 35 (wt/wt) % peracid solution and preferably from 6 to 12 (wt/wt) % peracid solution for a time sufficient to permit contact of the vapor with all surfaces of the article being sterilized, packaged or unpackaged. The total pulsed contact exposure time is preferably from 5 to 30 minutes with packaged articles. For temperature-sensitive articles, the peracid exposure can be carried out at a temperature of from 20 to 80° C. and preferably from 40 to 60° C. Treatment at higher temperatures is possible for articles that can tolerate them.

Some peracids in certain concentrations are explosive at elevated temperatures. For this reason, peracetic acid is usually transported and stored in aqueous solutions having less than 35 wt. % peracetic acid. The peracetic acid solution is easily vaporized, and effective treatment of articles at room temperature, according to this invention, can be achieved by exposing the articles to peracetic acid vapors at partial pressures in the range of from 0.2 to 18 torr. The lower pressure limit is the lower range limit of the effective concentration of the peracetic acid, and the upper limit is the saturation vapor pressure at room temperature. If the article to be sterilized can tolerate higher temperatures, then the pressure range will change accordingly.

After the pulsed treatment, the mixture gas carrying the antimicrobial agent is removed by evacuating the sterilization chamber. Plasma gas is then introduced into the sterilization chamber to sterilize the article inside.

The particular pulse-vacuum sequence order can be reversed as desired during successive repetitions of the pulsed treatment and plasma treatment cycle.

In the preferred process of this invention, the pulsed antimicrobial agent pretreatment is carried out with vapor introduced into the sterilizing chamber, and the article is pretreated with the peracid prior to exposing the article to the plasma. Suitable plasma sterilizing systems for carrying out the process of this invention are described in U.S. Pat. Nos. 5,115,166 and 5,178,829. The entire contents of these are incorporated herein by reference.

The process of this invention uses a plasma made from gas mixtures containing argon, helium and/or nitrogen; and oxygen and/or hydrogen, optionally containing inert gases and carbon dioxide. Nitrogen is not preferred because it can form toxic residues. The exhaust gas products fully satisfy current environmental and worker safety concerns, the products of the plasma being almost entirely water vapor, carbon dioxide and non-toxic gases normally found in the atmosphere.

Generally, a plasma is generated with an initial large component of high energy ions and ultraviolet (UV) emission as a matter of course. As the plasma is transported down stream and out of the plasma generating energy field, the charged particles recombine by collision with container surfaces to form uncharged energized free radicals, atoms and molecules.

An important feature of the present invention is to avoid the use of plasma having a large component of ions and ultraviolet emissions to effect sterilization. Instead, uncharged species of oxidizing or reducing agents, made highly reactive by activation with the plasma, are used to effect sterilization by a chemical process.

The apparatus disclosed herein is capable of producing plasma having uncharged, highly reactive species. For example, in the plasma generating chamber, oxygen is energized by microwave radiation and forms a plasma having an initial high concentration of ions and ultraviolet emissions. These are not allowed into the sterilization chamber as they tend to be strongly corrosive on the article to be sterilized, or the packaging. The UV emissions are localized in the plasma generating chamber and are attenuated by the restriction means and the plasma distribution means before they reach the sterilizing chamber. Similarly, as high energy ions hit the restrictive means and the internal walls of the plasma distribution means, they recombine with free electrons to revert to highly reactive uncharged atoms and radicals. By the time the plasma enters the sterilizing chamber, the plasma's downstream products consist essentially of energized and highly reactive uncharged free radicals and electronically excited uncharged atoms and molecules.

Typically, a microwave source is used to generate the plasma. It is channeled by a waveguide to form a highly confined EM field zone. Little of that field can spread to the sterilizing chamber. Thus, production of high energy ions and UV is only possible in the field region of the plasma generating chamber and not outside of it. Also, there is no EM field to cause non-uniformity in the sterilizing chamber. The restriction means of Applicants' apparatus, apart from obstructing the passage of UV and ions as noted above, further helps to make plasma generation outside the plasma generating chamber less favorable. The restriction means maintains an optimal gas pressure in the plasma generating chamber for generating plasma. Once the gas exits via the restriction means, the pressure drops to make generation difficult under normal conditions even if the EM field of the microwave source extended into this region. Thus, UV and ions can only be generated in the plasma generating chamber; once outside, they are allowed to dissipate to form a downstream plasma consisting essentially of energized, highly reactive uncharged free radicals, atoms and molecules.

Under these conditions, effective sterilization is effected without significant deterioration of packaging materials in which articles to be sterilized may be placed.

One suitable apparatus is. shown in FIG. 1. FIG. 1 is a top view and FIG. 2 is a front view of a single waveguide plasma sterilizer embodiment of this invention. The plasma sterilizer has a plasma generator 2 and a sterilizing chamber 4. The plasma generator 2 comprises an electromagnetic field generator such as a magnetron 6 and a waveguide 8 which directs the electromagnetic field. The plasma source gases are directed into plasma generating and delivering tubes 10, 12, and 14 by feeder tubes from gas delivery tubes 16, 18 and 20 leading from the control valve complex 22. Individual gases are fed from the pressured gas sources (not shown) by inlet lines 24, 25 and 26. The operation of the control valves in valve complex 22 is controlled by the central processing unit (CPU) 28 by standard procedures. The control valves and CPU can be any of the conventional, standard devices used for gas flow control in plasma generating equipment.

The sterilizing chamber 4 comprises top plate 30, side plates 32 and 34, bottom plate 36, back plate 37 and front sealing door 38 through which articles or materials to be sterilized are placed in the chamber. The plates are attached together in a sealed relationship to form a vacuum chamber, such as by welding. The door 38 is secured in a sealed relationship with the sterilizing chamber. It is hinged at the top, side or bottom with conventional hinge pins (structure not shown) to swing against abutting surfaces and an O-ring seal 40 (FIG. 3) of the side, top and bottom plates, where the pressure difference between the internal chamber vacuum pressure and the surrounding atmospheric pressure holds it tightly in place.

The plates and door can be made of any material having the strength required to withstand the external atmospheric pressure when the chamber is evacuated. Stainless steel or aluminum plates and door are preferred. The internal surface material of the chamber is critical and greatly affects the number of killing species available in the chamber. A suitable material is pure (98%) aluminum which can be applied either as a liner or as a flame-sprayed coating on all internal walls of the stainless steel chamber. An alternate material is nickel. An optimum material is an inert polymer such as polytetra-fluoroethylene (TEFLON).

Antimicrobial additives are added as a liquid or vapor through conduit 35 to inlet port 39 (FIG. 4).

The gases are exhausted from the sterilizing chamber through exhaust outlet port 42 to a conventional vacuum pump system (not shown).

FIG. 3 is a top cross-sectional view of the plasma sterilizer embodiment of FIG. 1 and FIG. 2, taken along the line 3—3 in FIG. 2. FIG. 4 is a side cross-sectional view of the plasma sterilizer embodiment of FIG. 1 and FIG. 3, taken along the line 4—4 in FIG. 3. Each of the plasma generators 10, 12 and 14 comprise an inlet cap 44 with gas inlet ports 46, 48 and 50 leading to a respective gas generator tube 51, 52 or 53 leading through the waveguide 8. In the waveguide 8, the gases are energized and convert in tubes 51, 52 and 53 to a plasma. The gas generator tube directs the plasma flow into the gas distribution tubes 54, 56 and 58 from which the plasma is fed into the sterilizing chamber 60. The gas generator tubes are enclosed in tubular metal cooling tubes 62 and 64. The caps 44 and the cooling tubes 62 and 64 are preferably provided with grooves or cooling fins (not shown) in a conventional manner to increase their efficiency in removing heat from gas generator tubes.

The distal end of tubes 51, 52 and 53 have increased thickness and forms a smooth surfaced venturi restriction 96 of reduced cross-sectional area. Cap 98 positioned on the proximal end of plasma distribution tube 56 has a preselected restrictive opening 99 of further reduced cross-sectional area. These restrictions are critical aspects of the preferred embodiment of this invention, creating a pressure difference between the low pressure plasma generating zone 87 and the vacuum pressure in the distribution tube 56 and sterilizing chamber 60, thereby allowing the operating pressures in the two chambers to be independently optimized.

The diameter of the restrictive opening 99 is selected to maintain a back pressure of from 0.1 to 150 torr and preferably from 1 to 40 torr in the plasma generating zone, with a vacuum chamber pressure in the range of from 0.01 to 100 torr and preferably from 0.1 to 15 torr. This pressure provides optimum energy transfer from the electromagnetic field to the gases with gas mixtures containing oxygen; argon, helium and/or nitrogen; and/or hydrogen and is a major factor for the production of a high yield of plasma at a minimum temperature and with the minimum power requirement achieved with the device of this invention. For most operating parameters, the restriction 99 can have a diameter of from 4.82 to 8.00 mm and preferably from 6.28 to 6.54 mm. These dimensions may also vary if gas flows, vacuum system or the conductance of the gas distribution system changes.

The distal ends of the gas distribution tubes 54, 56 and 58 are supported by spring-biased end supports 66 mounted on sideplate 32.

The door 38 is held in sealing engagement by atmospheric pressure against the O-ring seal 40 mounted in the flange 41 extending from the side plates 32 and 34, and the top and bottom plates 30 and 36 (not shown). Optionally, additional conventional closure clamps or latches can be used to insure closure of the door before chamber evacuation is initiated.

FIG. 5, FIG. 6 and FIG. 7 are cross-sectional views of gas distribution tubes 54, 58 and 56, respectively, showing angular positions of the gas distribution outlet ports. The outlet ports are positioned to provide plasma flow to all lower portions of the sterilizing chamber 60 where articles to be sterilized are placed. Tube 54 shown in FIG. 5 is placed adjacent back plate 37 and directs plasma gases downward and toward the lower center of the chamber through outlet ports 70 and 72, respectively. Tube 58 shown in FIG. 6 is placed adjacent the door 38 and directs plasma gases downward and toward the lower center of the chamber through outlet ports 74 and 76, respectively. Tube 56 shown in FIG. 7 is placed in the central portion of the chamber 60 and directs plasma gases laterally downward through outlet ports 78 and 80. The outlet ports shown for the distribution tubes are representative and can be changed to any other configuration which achieves optimal plasma distribution to the sterilizing zone or zones of the chamber. Although only one angular arrangement is shown, each tube can have more than one angular set of outlet ports, each having different angles, along the length of the tube, as desired. The choice of outlet port angles and locations should be selected in view of how the articles to be sterilized are to be placed in the chamber and the type of article to be sterilized.

The plasma is directed through a change of direction, preferably at least 90°, before discharging it into the sterilizing chamber. This prevents direct impingement of hot plasma onto the articles being sterilized. The gas distributors also allow ions to recombine by collisions with their surfaces and block the UV radiation.

The apparatus can be used to generate a sterilizing plasma from a mixture of oxygen; argon, helium, and/or nitrogen; and hydrogen, or with a mixture of air and hydrogen, supplemented by oxygen or nitrogen to give the desired ratios. The sterilization is carried out at a vacuum pressure of from 0.01 to 15 torr and preferably from 1 to 15 torr. Sterilization may be carried out at higher pressures provided steps are taken to ensure uniformity of gas flows and temperature throughout the chamber. The temperature in the sterilizing chamber is maintained below 80° C. and preferably from 38 to 60° C. for articles that can not tolerate high temperatures. Elevated temperatures may preferably be used with articles capable of withstanding them.

Typically, a microwave source is used to generate the plasma. It is channeled by a waveguide to form a highly confined electromagnetic (EM) field zone. Little of that field can spread to the sterilizing chamber. Thus, production of high energy ions and UV is only possible in the field region of the plasma generating chamber and not outside of it. Also, there is no EM field to cause non-uniformity in the sterilizing chamber. The restriction means, apart from obstructing the passage of UV and ions as noted above, further helps to make plasma generation outside the plasma generating chamber less favorable. The restriction means maintains an optimal gas pressure in the plasma generating chamber for generating plasma. Once the gas exits via the restriction means, the pressure and the EM field drop to make generation difficult under normal conditions. Thus, UV and ions can only be generated in the plasma generating chamber; once outside, they are allowed to dissipate to form a downstream plasma consisting essentially of energized, highly reactive uncharged free radicals, atoms and excited molecules.

Under these conditions, effective sterilization is effected without significant deterioration of packaging materials in which articles to be sterilized may be placed.

Following pulsed treatment with antimicrobial agent, the sterilizing chamber is evacuated to a pressure of less than 10 torr. The article is then exposed to a plasma generated from a gaseous mixture of argon, helium or nitrogen mixed with oxygen and/or hydrogen at temperatures of less than 60° C., a pressure of from 0.01 to 100 torr, preferably from 0.1 to 15 torr and a treatment time of at least 5, and preferably from 10 to 15 minutes. For sterilizing packaged goods, the gas mixtures from which the plasma is generated can contain from 1 to 21 (v/v) % oxygen and from 1 to 20 (v/v) % hydrogen, the balance being argon, helium and/or nitrogen and optional small quantities of inert gases.

It is to be understood that the operating temperature of the present process is determined by the characteristics of the articles being sterilized, not by temperature limitations of the sterilization process. Many medical devices will not withstand temperature over 60° C., while other articles such as metallic surgical instruments are more efficiently sterilized at higher temperatures.

Similarly, the pressure limitations given are examples illustrative of the preferred embodiments. Different pressure limits are contemplated for other plasma generating chambers or sterilizing chambers having different dimensions or surface characteristics.

The gas mixtures producing plasmas for sterilizing packages preferably contain from 1 to 10 (v/v) % oxygen and from 2 to 8 (v/v) % hydrogen, and optimally contain from 2 to 8 (v/v) % oxygen and from 3 to 7 (v/v) % hydrogen. Packages are treated for at least 15 minutes and preferably from 1 to 5 hours.

In an optimum method of sterilizing, the articles to be sterilized are placed in the sterilizing chamber, supported by conventional fixtures which permit the plasma gas products to reach all surfaces of the articles.

1. The chamber is closed. The sterilizing chamber is evacuated to a pressure of 0.1 torr, and an isolation valve between the vacuum pump and sterilizing chamber is closed.

2. Antimicrobial agent in the form of a pulse of vaporized peracetic acid in a gaseous mixture with argon and/or water vapor as a carrier gas is admitted into the chamber. The peracetic acid vapor has a concentration of at least 0.1 mg/L peracetic acid. Alternatively, a pulse of vaporized hydrogen peroxide in a gaseous mixture with argon as a carrier gas is introduced into the chamber. The hydrogen peroxide vapor has a concentration of at least 0.1 mg/L hydrogen peroxide. If peracetic acid pretreatment is to be combined with hydrogen peroxide pretreatment, vaporized peracetic acid and hydrogen peroxide in a gaseous mixture with argon and/or water vapor as a carrier gas is admitted into the chamber. The peracetic acid vapor has a concentration of 0.1 mg/L peracetic acid. The hydrogen peroxide vapor has a concentration of at least 0.1 mg/L hydrogen peroxide. The pulse of vaporized peracetic acid and/or hydrogen peroxide vapor exposure is continued for from 5 to 30 minutes.

3. The pressure in the sterilizing chamber is reduced to less than 2 torr for from 1 to 2 minutes.

4. Steps 2 and 3 are repeated 4 times, and the chamber is evacuated until a predetermined amount, preferably at least 90% of the antimicrobial agent has been removed.

5. Process gases are admitted to the plasma chamber, preferably at a flow rate of up to 5 liters per minute, and optimally from 3 to 4 liters per minute.

6. The magnetron is energized to create the plasma, and the plasma products flow into the sterilizing chamber.

7. The plasma treatment is continued for from 5 to 30 minutes and preferably from 5 to 15 minutes.

8. The magnetron is deactivated and the process gas flow to the plasma chamber is terminated.

9. Steps 1–8 are repeated until sterilization is complete and all spores are killed. Hydrogen peroxide and peracetic acid treatments can be alternated so that the pretreatment is limited to either one for a particular cycle repetition.

10. The isolation valve between the pump and chamber is closed, and the chamber is vented to the atmosphere. The sterilizing chamber can be pumped down and partially vented to remove acidic vapors before being fully vented to the atmosphere.

The above method sterilizes effectively in less time than is required without the pulsed antimicrobial agent treatment.

The remaining reactive plasma components have a short life, and quickly decay to form water vapor (gas), carbon dioxide, and other non-toxic components usually found in air. These are fully acceptable as residues or as exhaust gas components.

One application of the present invention is to sterilize lyophilizers. Lyophilizers are essentially large vacuum chambers (e.g., 5 to 30 cubic ft.) used to freeze dry solutions or liquid suspensions. In the medical industry they are used primarily to freeze dry pharmaceuticals for preservation.

FIG. 8 is a schematic illustration of a lyophilizer adapted to be sterilized by the plasma process of the present invention. The lyophilizer system 300 includes a lyophilizer chamber 312, a condenser 314 and a vacuum pump 316. The vacuum pump 316 is capable of evacuating the lyophilizer chamber 312 via a vacuum line 322, the condenser 314 and another vacuum line 324. Typically, the material or articles to be dried (which may be frozen) are held in containers and loaded into the lyophilizer chamber 312. After the door or the lyophilizer chamber (not shown) is sealed, the interior of the lyophilizer is evacuated using the vacuum pump 316. The material or articles cool (and freeze, if they are not already frozen) as water evaporates. The evaporated water is mostly condensed by the condenser 314 and removed. Further pumping causes water in the material or articles to sublime until substantially all the water is removed. When the process is complete, the lyophilizer chamber 312 is vented and the containers are removed.

Lyophilizers used to prepare pharmaceuticals must have their interior chamber sterilized after each batch operation. Conventional methods of using heat or ethylene oxide are problematic. As mentioned earlier, ethylene oxide is a carcinogen and great precautions must be exercised in its use. Adapting the lyophilizer to steam sterilization raises considerations such as condensation problems and the ability of the lyophilizer to withstand high temperature (e.g., 121° C.) and high internal pressure (e.g., 15 psig).

According to one aspect of the present invention, a plasma generating system 330 includes a plasma generating chamber 332. The lyophilizer chamber is connected to receive a gas plasma from the plasma generating chamber 332 via a port 340 and connecting tube 342. During the plasma sterilization process, the lyophilizer chamber acts as a sterilizing chamber with the evacuation provided by the vacuum pump 316.

In one embodiment, the interior of the lyophilizer system is sterilized by the process of the invention. In another embodiment, both the interior of the lyophilizer system and the material or articles therein after completion of lyophilization are subjected to the process of the invention for sterilization.

For a large capacity lyophilizer, distributing gas plasma via a single port or location to the interior of the lyophilizer chamber 312 may led to nonuniformity. One or more internally fitted gas distributors such as that shown in FIGS. 3, 4 are preferable. In other embodiments, additional ports such as 340', 340" and 340'" and additional connecting tubes such as 342', 342" and 342'" connected to the plasma generating chamber 332 are used to introduce the gas plasma into various regions of the lyophilizer chamber 312.

The antimicrobial agent discussed previously is introduced from an antimicrobial agent source 350 through a line 352 into the lyophilizer chamber 312 via one or more of the ports and connecting tubes. In this way, the process of the aforementioned invention can be practiced.

FIG. 9 is a schematic illustration of a general enclosure adapted to be sterilized by the plasma process of the present invention. The enclosure 412 is a rigid structure able to withstand evacuation. It has one or more inlet ports, such as 440, 440', 440'", and one or more outlet ports such as 426, 426'. A vacuum pump 416 is capable of evacuating the enclosure 412 through one or more of the outlet ports such as 426, 426' via vacuum lines such as 424, 424'.

The antimicrobial agent is introduced from an antimicrobial agent source 450 through a line 452 into the enclosure 412 via one or more of the inlet ports and connecting tubes such as 442, 442', 442", 442'".

A plasma generating system 430 includes a plasma generating chamber 432 in which plasma is generated from a gas mixture by coupling of energy into it. A suitable plasma generating system has previously been disclosed. Another suitable plasma generating system has also been disclosed in U.S. Pat. No. 5,115,166, the entire content thereof is incorporated herein by reference. The enclosure 412 is connected to receive a gas plasma from the plasma generating chamber 432 via one or more of the inlet ports and connecting tubes such as 442, 442', 442", 442'".

In this way, the enclosure illustrated in FIG. 9 is capable of being sterilized by exposure to antimicrobial agent as well as to a plasma gas.

While the embodiments of the various aspects of the present invention that have been described are the preferred implementation, those skilled in the art will understand that variations thereof may also be possible. Therefore, the invention is entitled to protection within the scope of the appended claims.

What is claimed is:

1. A process for plasma sterilization of an interior of a chamber and any articles therein, comprising:

exposing said interior of said chamber and any articles therein to at least one combination sterilizing cycle, each combination sterilizing cycle comprising:

a pulsed treatment with gaseous antimicrobial agent, said pulsed treatment comprising one or more pulse-vacuum cycles, each pulse-vacuum cycle comprising the steps of evacuating said chamber and exposing the interior of said chamber and any articles therein to gaseous antimicrobial agent for a predetermined duration;

removing the antimicrobial agent after the pulsed treatment by evacuating said chamber; and a plasma treatment comprising exposing the interior of said chamber and any articles therein to a stream of plasma, said plasma being generated in a separate plasma generating chamber and being supplied to effect sterilization in said chamber.

2. The process of claim 1, wherein the antimicrobial agent is selected from the group consisting of hydrogen peroxide, a peracid antimicrobial agent, or mixtures thereof, the peracid antimicrobial agent being selected from the group consisting of saturated and unsaturated peralkanoic acids having from 1 to 8 carbon atoms and halogenated derivatives thereof.

3. A. The process of claim 2 wherein the peracid antimicrobial agent is peracetic acid.

4. The process of claim 2 wherein the antimicrobial agent is halogenated peracetic acid.

5. The process of claim 2 wherein the antimicrobial agent is hydrogen peroxide.

6. The process of claim 2 wherein the antimicrobial agent is a mixture of peracetic acid and hydrogen peroxide.

7. The process of claim 1, wherein the pulsed treatment and the plasma treatment in each combination sterilizing cycle follow a predetermined order.

8. The process of claim 1, wherein the pulsed treatment is preceded by a plasma treatment.

9. The process of claim 1, wherein the step of exposing the article to gaseous antimicrobial agent for a predetermined duration includes ramping the pressure of the gaseous antimicrobial agent.

10. The process of claim 1, wherein the gaseous antimicrobial agent is carried in a gaseous mixture with a nonreactive carrier gas.

11. The process of claim 10, wherein the gaseous antimicrobial agent in the gaseous mixture has a partial pressure of from 0.1 to 50 torr, and the gaseous mixture with the antimicrobial agent is removed after the pulsed treatment by evacuating said chamber until a predetermined amount of the antimicrobial agent has been removed.

12. The process of claim 10, wherein the gaseous antimicrobial agent in the gaseous mixture in said chamber is maintained at a predetermined temperature and at partial pressures up to a maximum concentration of antimicrobial agent supported by said temperature maintained in said chamber.

13. The process of claim 10 wherein the antimicrobial agent is selected from the group consisting of hydrogen peroxide, a peracid antimicrobial agent, or mixtures thereof, the peracid antimicrobial agent being selected from the group consisting of saturated and unsaturated peralkanoic acids having from 1 to 8 carbon atoms and halogenated derivatives thereof.

14. The process of claim 10 wherein the peracid antimicrobial agent is peracetic acid.

15. The process of claim 10 wherein the antimicrobial agent is halogenated peracetic acid.

16. The process of claim 10 wherein the antimicrobial agent is hydrogen peroxide.

17. The process of claim 10 wherein the antimicrobial agent is a mixture of peracetic acid and hydrogen peroxide.

18. The process of claim 10 wherein the gaseous mixture additionally includes water vapor.

19. A process for plasma sterilization of an interior of a chamber and any articles therein, including:
    exposing said interior of said chamber and any articles therein to at least one combination sterilizing cycle, each combination sterilizing cycle comprising:
    an antimicrobial pretreatment by exposing said interior of said chamber and any articles therein to gaseous antimicrobial agent;
    removing the antimicrobial agent from said chamber; and
    exposing said interior of said chamber and any articles therein to a stream of plasma, said plasma being generated in a separate plasma generating chamber.

20. The process of claim 19, wherein the gaseous antimicrobial agent is carried in a gaseous mixture with a nonreactive carrier gas.

21. The process of claim 20, wherein the gaseous antimicrobial agent in the gaseous mixture has a partial pressure of from 0.1 to 50 torr, and the gaseous mixture with the antimicrobial agent is removed after the pulsed treatment by evacuating said chamber until a predetermined amount of the antimicrobial agent has been removed.

22. An enclosure adapted for sterilization therein, comprising:
    one or more inlet ports;
    one or more outlet ports;
    a vacuum pump connectable to at least one of said outlet ports of the enclosure for evacuating the enclosure;
    an antimicrobial agent source connectable to at least one of said inlet ports of the enclosure for introducing an antimicrobial agent therein; and
    a plasma generating system connectable to at least one of said inlet ports of the enclosure for introducing a plasma therein.

23. An enclosure adapted for sterilization therein as in claim 22, wherein the enclosure is a sterile isolation enclosure.

24. An enclosure adapted for sterilization therein as in claim 22, wherein the enclosure is a lyophilizer.

25. An enclosure adapted for sterilization therein as in claim 22, wherein the enclosure contains at least one article.

26. A sterilization system, comprising:
    an enclosure for sterilizing therein, said enclosure having one or more inlet ports and one or more outlet ports;
    a vacuum pump connectable to at least one of said outlet ports of the enclosure for evacuating the enclosure;
    an antimicrobial agent source connectable to at least one of said inlet ports of the enclosure for introducing an antimicrobial agent therein; and
    a plasma generating system connectable to at least one of said inlet ports of the enclosure for introducing a plasma therein.

27. A sterilization system as in claim 26, wherein the enclosure is a sterile isolation enclosure.

28. A sterilization system as in claim 26, wherein the enclosure is a lyophilizer.

29. A sterilization system as in claim 26, wherein the enclosure contains at least one article.

* * * * *